US009550074B2

(12) United States Patent
Saito et al.

(10) Patent No.: US 9,550,074 B2
(45) Date of Patent: Jan. 24, 2017

(54) LASER TREATMENT DEVICE (71) Applicant: ANRITSU CORPORATION, Kanagawa (JP)

(72) Inventors: Masahiro Saito, Kanagawa (JP); Yoshihiro Ino, Kanagawa (JP)

(73) Assignee: ANRITSU CORPORATION, Kanagawa (JP)

( * ) Notice: Subject to any disclaimer, the term of this patent is extended or adjusted under 35 U.S.C. 154(b) by 71 days.

(21) Appl. No.: 14/425,624

(22) PCT Filed: Apr. 7, 2014

(86) PCT No.: PCT/JP2014/001988
§ 371 (c)(1),
(2) Date: Mar. 3, 2015

(87) PCT Pub. No.: WO2014/167829
PCT Pub. Date: Oct. 16, 2014

(65) Prior Publication Data
US 2015/0224333 A1   Aug. 13, 2015

(30) Foreign Application Priority Data

Apr. 10, 2013   (JP) ................................ 2013-081916

(51) Int. Cl.
*A61N 5/06* (2006.01)
*A61B 18/20* (2006.01)
*A61N 5/067* (2006.01)

(52) U.S. Cl.
CPC .............. *A61N 5/062* (2013.01); *A61B 18/20* (2013.01); *A61N 2005/067* (2013.01); *A61N 2005/0626* (2013.01)

(58) Field of Classification Search
None
See application file for complete search history.

(56) References Cited

U.S. PATENT DOCUMENTS

2012/0283710 A1*  11/2012  Liu ...................... A61B 18/203
                                                        606/9

FOREIGN PATENT DOCUMENTS

JP           2006-087646 A      4/2006

* cited by examiner

*Primary Examiner* — Brian T Gedeon
(74) *Attorney, Agent, or Firm* — McDermott Will & Emery LLP (57) ABSTRACT

A laser therapy apparatus includes: a laser source including a light source for outputting first laser light; a laser irradiator for subjecting the first laser light to at least one of light-guiding and beamforming to convert the first laser light into second laser light, and radiating the second laser light to the exterior; a second light amount detector for detecting a light amount of second laser light; a pre-use checker for performing a pre-use check at least based on a result of detection by the second light amount detector; a pre-use check detector for determining whether a pre-use check corresponding to the current activation has been performed or not, based on past-activation information and a result of the check by the pre-use checker; and an alarm for, at the current activation, reporting a result of determination by the pre-use check detector.

18 Claims, 6 Drawing Sheets

LASER TREATMENT DEVICE

RELATED APPLICATIONS

This application is a national phase of International Application No. PCT/JP2014/001988, filed on Apr. 7, 2014, which in turn claims the benefit of Japanese Application No. 2013-081916, filed on Apr. 10, 2013 the disclosures of which Applications are incorporated by reference herein.

TECHNICAL FIELD

The present application relates to a laser therapy apparatus.

BACKGROUND ART

Laser is used for various kinds of therapy. For example, laser therapy apparatuses are used in photodynamic therapy (hereinafter abbreviated as "PDT").

PDT is a localized therapy which utilizes a photochemical reaction based on a photosensitive substance which abundantly accumulates in cancer cells as well as laser light irradiation. Specifically, in this therapy, a photosensitive substance (e.g., talaporfin sodium) is administered in vivo, and the cancer cells in which the photosensitive substance has accumulated are irradiated with laser light of an excitation wavelength which is specific to that photosensitive substance, thus generating singlet oxygens from the photosensitive substance, and allowing these singlet oxygens to destroy the cancer cells.

For example, a laser therapy apparatus for use in PDT is proposed in Patent Document 1.

CITATION LIST

Patent Literature

[Patent Document 1] Japanese Laid-Open Patent Publication No. 2006-87646

SUMMARY OF INVENTION

Technical Problem

When conducting therapy such as PDT, it is preferable to minimize situations where malfunctioning of a laser therapy apparatus during therapy makes it impossible to continue the therapy.

The present application aims to provide a laser therapy apparatus which, during therapy, allows a user to confirm the existence of a state where laser therapy can be appropriately conducted.

Solution to Problem

A laser therapy apparatus according to an embodiment of the present application, comprises: a laser source including at least one light source for outputting first laser light; a laser irradiator for subjecting the first laser light to at least one of light-guiding and beamforming to convert the first laser light into second laser light, and radiating the second laser light to the exterior; a second light amount detector for detecting a light amount of second laser light; a pre-use checker for performing the pre-use check at least based on a result of detection by the second light amount detector; a pre-use check detector for determining whether a pre-use check corresponding to a current activation has been performed or not, based on past-activation information and a result of the check by the pre-use checker; and an alarm for, at the current activation, reporting a result of determination by the pre-use check detector.

Advantageous Effects of Invention

With a laser therapy apparatus according to the present application, it is possible to confirm the existence of a state where laser therapy can be appropriately conducted.

DESCRIPTION OF EMBODIMENTS

In outline, one implementation of the present invention is as follows.

A laser therapy apparatus according to one implementation of the present invention comprises: a laser source including at least one light source for outputting first laser light; a laser irradiator for subjecting the first laser light to at least one of light-guiding and beamforming to convert the first laser light into second laser light, and radiating the second laser light to the exterior; a second light amount detector for detecting a light amount of second laser light; a pre-use checker for performing a pre-use check at least based on a result of detection by the second light amount detector; a pre-use check detector for determining whether a pre-use check corresponding to a current activation has been performed or not, based on past-activation information and a result of the pre-use check by the pre-use checker; and an alarm for, at the current activation, reporting a result of determination by the pre-use check detector.

The past-activation information may be information of an immediately previous activation of the current activation; and the pre-use check detector may determine whether the pre-use check has been performed or not based on information of the immediately previous activation of the current activation.

The pre-use check detector may determine that a pre-use check corresponding to the current activation has been performed if the pre-use check was performed at the immediately previous activation of the current activation; and that a pre-use check corresponding to the current activation has not been performed if the pre-use check was not performed at the immediately previous activation of the current activation.

The pre-use check detector may determine that no pre-use check corresponding to the current activation has been performed if a predetermined period or more has elapsed since the immediately previous activation and until the current activation, regardless of whether the pre-use check was performed at the immediately previous activation or not.

The past-activation information may be information of a predetermined plurality of consecutive past activations including the immediately previous activation of the current activation; and the pre-use check detector may determine whether a pre-use check corresponding to the current activation has been performed or not based on information of the plurality of past activations.

The past-activation information may be information of a plurality of past activations including the immediately previous activation of the current activation which were made within a predetermined past period from the current activation; and the pre-use check detector may determine whether a pre-use check corresponding to the current activation has been performed or not based on information of the plurality of past activations.

The pre-use check detector may determine whether a pre-use check corresponding to the current activation has been performed or not based on whether the second laser light was radiated between the activation among the plurality of past activations at which the pre-use check was performed and the current time.

The pre-use check detector may determine whether a pre-use check corresponding to the current activation has been performed or not based on a total length of time for which the second laser light was radiated between the activation among the plurality of past activations at which the pre-use check was performed and the current time.

If the result of detection by the second light amount detector satisfies a predetermined criterion which is provided in advance, the pre-use checker may determine that a state exists where second laser light suitable for therapy is emittable from the laser irradiator.

The pre-use check by the pre-use checker may comprise a check as to whether a state exists where second laser light suitable for therapy is emittable from the laser irradiator.

The pre-use checker may determine that the laser therapy apparatus is malfunctioning if the result of detection by the second light amount detector does not satisfy a predetermined criterion which is provided in advance.

The laser therapy apparatus may further comprise a first light amount detector for detecting a light amount of first laser light, wherein the pre-use check by the pre-use checker may comprise a check as to whether a result of detection by the first light amount detector satisfies a predetermined criterion which is provided in advance.

The laser therapy apparatus may further comprise a current detector for detecting a current value of an electric current which is supplied to the light source, wherein the pre-use check by the pre-use checker may comprise a check as to whether a result of detection by the current detector satisfies a predetermined criterion which is provided in advance.

The laser therapy apparatus may further comprise a temperature detector for detecting a temperature of the light source, wherein the pre-use check by the pre-use checker may comprise a check as to whether a result of detection by the temperature detector satisfies a predetermined criterion which is provided in advance.

The laser therapy apparatus may further comprise: a first light amount detector for detecting a light amount of first laser light; a current detector for detecting a current value of an electric current which is supplied to the light source; and a temperature detector for detecting a temperature of the light source, wherein the pre-use checker may determine that the laser therapy apparatus has an anomaly if at least one of a result of detection by the first light amount detector, a result of detection by the current detector and a result of detection by the temperature detector does not satisfy the predetermined criterion.

The laser therapy apparatus may further comprise a operational interface for setting laser light output from the laser source ON or OFF.

The pre-use checker may control the laser source so as to output first laser light with a predetermined period and a predetermined output level when laser light output is set ON by the operational interface, and perform the pre-use check based on information during the predetermined period.

The laser source may include a plurality of light sources, and output the first laser light from each of the plurality of light sources.

The pre-use check detector may cause the alarm to report the check result of the pre-use check together with the result of determination by the pre-use check detector.

Hereinafter, with reference to the drawings, a laser therapy apparatus according to one implementation of an embodiment of the present application will be described in detail.

<<Regarding Construction>>

<Overall Construction>

Figure 1:
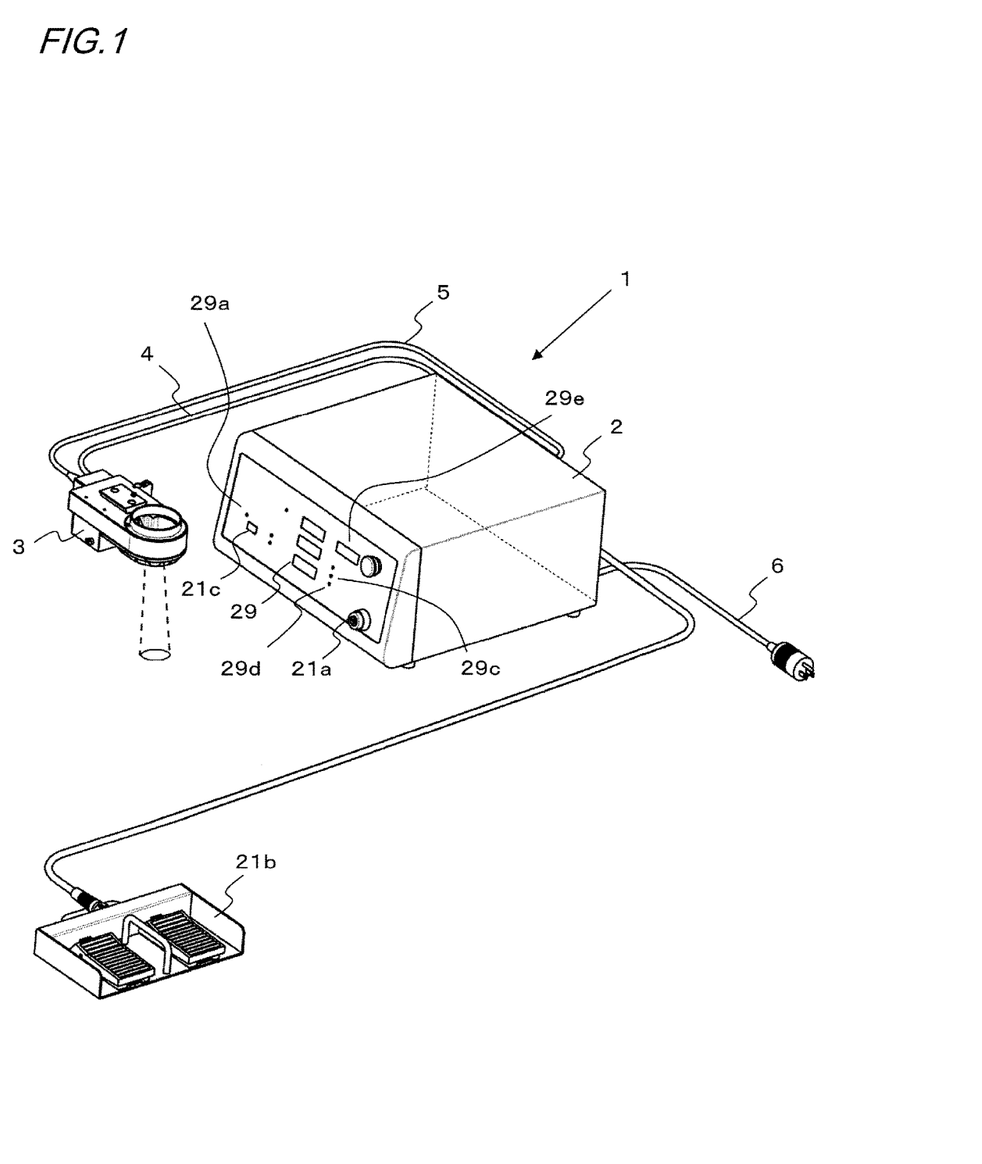
FIG. 1 An example outer view of a laser therapy apparatus according to Embodiment 1 of the present application.

FIG. 1 is an example outer view of a laser therapy apparatus according to the present embodiment.

As shown in FIG. 1, a laser therapy apparatus 1 includes a main body 2, an irradiation unit 3, a light-guiding fiber 4, a signal cable 5, and a power cable 6.

The laser therapy apparatus 1 operates in a pre-use check mode and a therapy mode. A "pre-use check" means checking whether laser light which is suitable for therapy is emittable at least from the irradiation unit 3. In the pre-use check mode, the laser therapy apparatus 1 performs a pre-use check of the laser therapy apparatus 1. In other words, the laser therapy apparatus 1 performs a check as to whether a state exists where laser light which is suitable for therapy can be radiated at least from the irradiation unit 3. In the therapy mode, in accordance with an instruction from a manipulator, the laser therapy apparatus 1 radiates laser light for therapy from the irradiation unit 3.

<Main Body 2>

Figure 2:
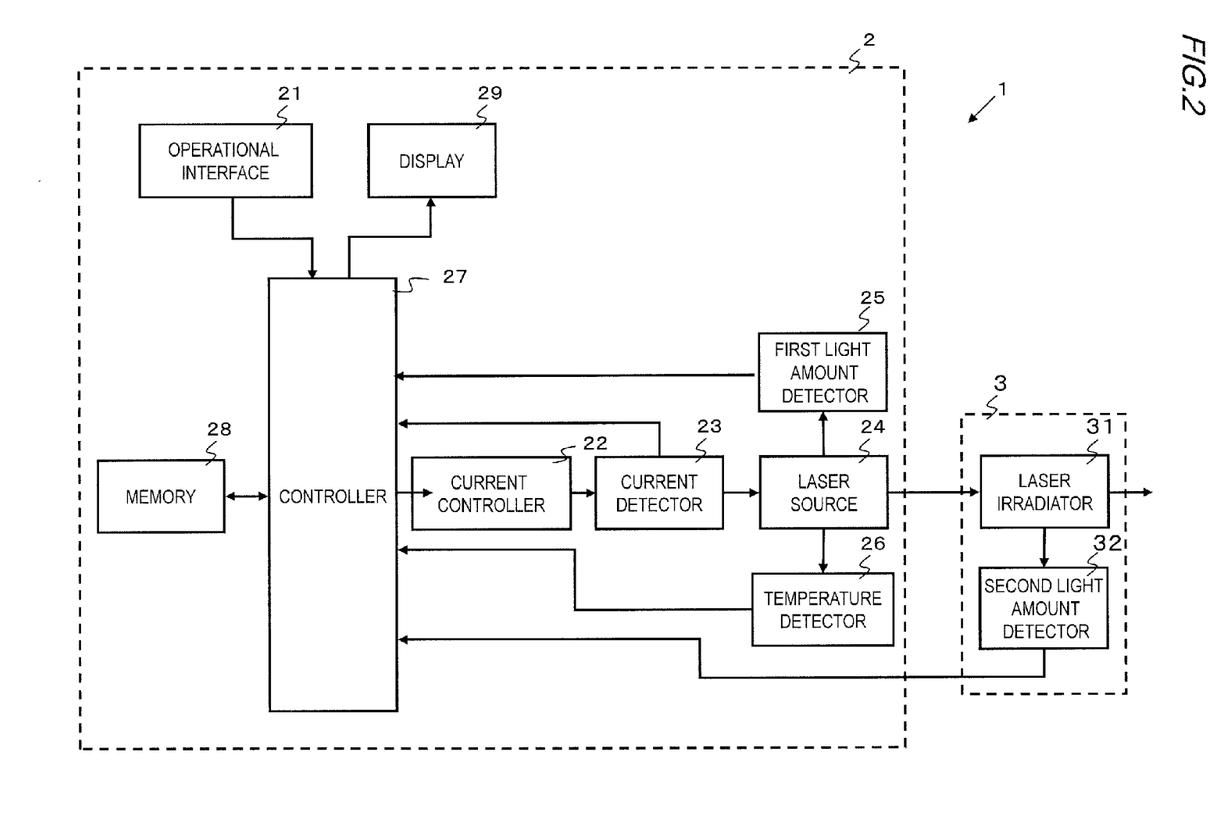
FIG. 2 An example block diagram of schematic hardware of the laser therapy apparatus according to Embodiment 1 of the present application.

FIG. 2 is a block diagram showing example schematic hardware construction of the laser therapy apparatus 1. As shown in FIG. 2, the main body 2 includes a operational interface 21, a current controller 22, a current detector 23, a laser source 24, a first light amount detector 25, a temperature detector 26, a controller 27, a memory 28, and a display 29. The controller 27 and the memory 28 are composed of a storage device, such as a memory, and a microcomputer or the like which includes an informational operation device such as a CPU, for example.

<Operational Interface 21>

As shown in FIG. 1, the operational interface 21 includes a power switch 21a, a foot switch 21b for switching ON/OFF laser light irradiation, and a pre-use check switch 21c for selecting the pre-use check mode. Further switches and input devices with which the user makes various settings for the laser therapy apparatus 1 may be included, e.g., output setting of laser light and irradiation time.

<Current Controller 22>

As the user turns laser light irradiation ON with the foot switch 21b, under control of the controller 27, the current controller 22 supplies an electric current of a predetermined output level to each of a plurality of light sources of the laser source 24, via the current detector 23.

<Current Detector 23>

In the pre-use check mode, the current detector 23 detects the current value of an actual electric current which is supplied from the current controller 22 to the light sources in the laser source 24, and outputs the result of detection to the controller 27. This current value is detected based on a voltage drop that is measured by using a resistor (not shown) which is included in the current detector 23, for example.

<Laser Source 24>

For example, the laser source 24 includes a plurality of light sources (not shown) for redundancy, and, based on an electric current which is supplied from the current controller 22, outputs laser light (hereinafter referred to as "first laser light") from the respective light sources. The light sources which are used herein are semiconductor laser devices, for example. The first laser light which is output from the laser source 24 is guided to the subsequently-described laser irradiator 31, via the light-guiding fiber 4.

Although the laser source 24 includes a plurality of light sources in the present embodiment, it is not necessary to provide a plurality of light sources; a single light source may instead be used.

Moreover, the wavelength and intensity of the first laser light which is emitted from the light sources may be determined based on the conditions of PDT, e.g., the site which is subject to therapy and the type of the photosensitive substance used. For example, the wavelength of the first laser light is 664 nm±2 nm, with an output of 265 mW±20%.

<First Light Amount Detector 25>

In the pre-use check mode, the first light amount detector 25 detects the respective light amounts of first laser light from two light sources of the laser source 24, and outputs the result of detection to the controller 27. Specifically, the first light amount detector 25 is composed of a photodiode (not shown) and an I-V (current-voltage) conversion circuit (not shown), and receives laser light at the photodiode and converts it to a current value, and also converts that current value to a voltage value at the I-V (current-voltage) conversion circuit. Then, it outputs a signal concerning this voltage value to the controller 27.

Note that each light source in the aforementioned laser source 24 is accommodated in a High Heat Load (hereinafter abbreviated as "HHL") package (not shown), such that each HHL package accommodates a photodiode of the first light amount detector 25 together with the light source. Then, the photodiode receives the light which leaks out into the HHL package when first laser light which is output from the light source is guided to the light-guiding fiber 4. The entire HHL package has a structure corresponding to an integrating-sphere, and a light amount which is proportional to the light amount of first laser light that is guided to the light-guiding fiber 4 can be incessantly detected at the first light amount detector 25 by means of the photodiode.

<Temperature Detector 26>

In the pre-use check mode, the temperature detector 26 detects the temperature of the laser source 24 while outputting first laser light, and outputs the result of detection to the controller 27. Specifically, a temperature thermistor is included as the temperature detector 26 in each HHL package, and the temperature within the HHL package is detected with this temperature thermistor, the result of this detection being output to the controller 27.

<Controller 27>

Based on various settings of the operational interface 21, the controller 27 controls each block in the main body 2 in the pre-use check mode and in the therapy mode. Control of each block occurs as software or firmware which defines a control procedure of each block is read from a memory, and consecutively executed by an information processing device, for example.

Specifically, when the pre-use check switch 21c of the operational interface 21 is turned ON by the user, the controller 27 controls each element under the pre-use check mode. Specifically, in response to the laser light output being turned ON by the user with the foot switch 21b, the laser source 24 is controlled so as to output laser light with a predetermined time and a predetermined output level which were set in advance. If the foot switch 21b is kept ON beyond the predetermined time which was set in advance by the user, the controller 27 exerts control of performing a pre-use check within that predetermined time, even if the laser light continues to be output. Alternatively, when the predetermined time has passed, the controller 27 stops laser light output even if the foot switch 21b remains ON, and exerts control of performing a pre-use check.

Moreover, when the laser therapy apparatus 1 is activated, the controller 27 outputs a signal indicating the activation to the memory 28. As will be described below, the laser therapy apparatus 1 is capable of operating in the therapy mode upon activation. In other words, the therapy mode is selected upon activation.

Figure 3:
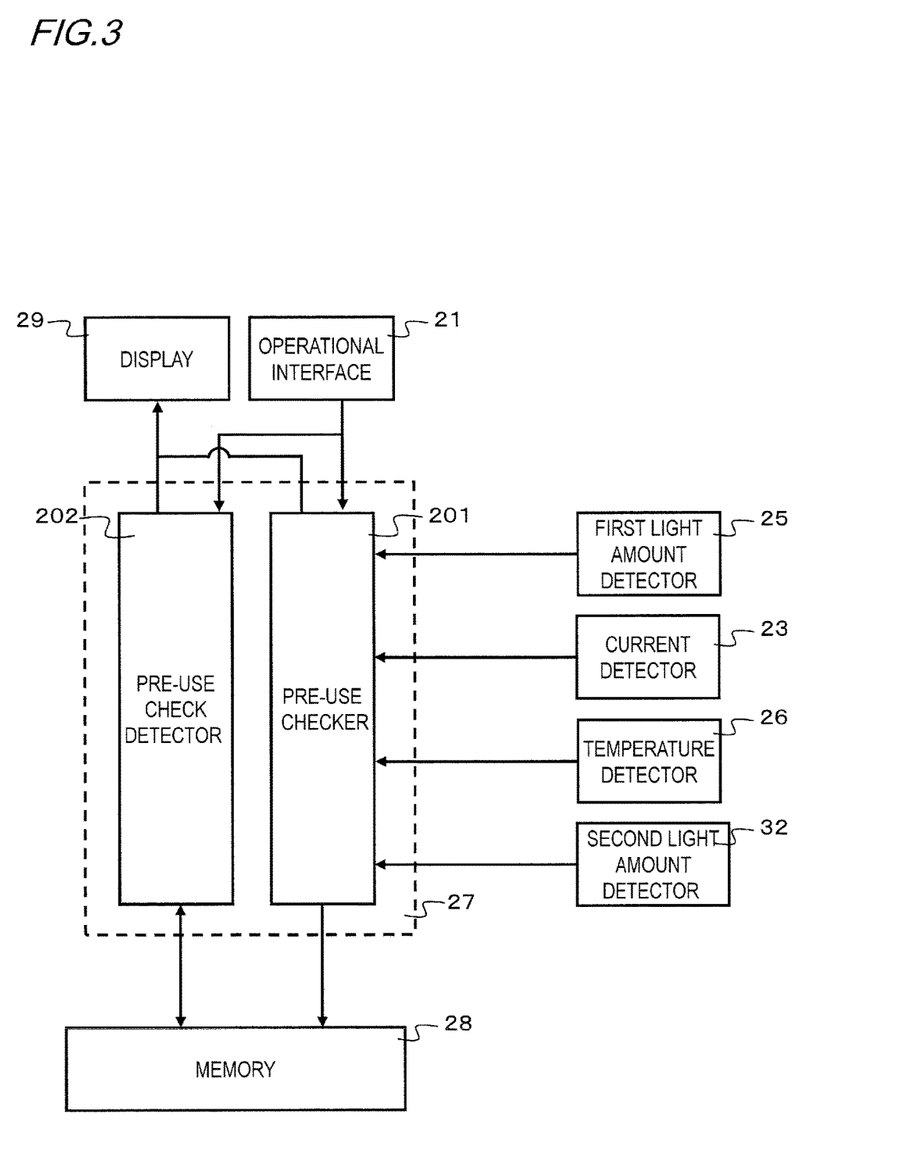
FIG. 3 An example detailed functional block diagram of a controller of the laser therapy apparatus according to Embodiment 1 of the present application.

When the pre-use check switch 21c is turned ON by the user so that the pre-use check mode is selected, the controller 27 switches the mode to the pre-use check mode to perform a pre-use check. FIG. 3 shows an example functional block diagram of the controller 27 concerning a pre-use check. The controller 27 includes a pre-use checker 201 and a pre-use check detector 202.

Note that, even when the "pre-use check mode" is selected at the operational interface 21, if the foot switch 21b becomes OFF before the predetermined time which was set in advance by the user lapses, the controller 27 does not detect that a pre-use check has been performed.

<Pre-Use Checker 201>

If the pre-use check mode is selected with the pre-use check switch 21c, and the foot switch 21b is kept ON for the predetermined time, the pre-use checker 201 receives results of detection from the current detector 23, the first light amount detector 25, the temperature detector 26, and the subsequently-described second light amount detector 32 corresponding to each light source, and determines whether these results of detection satisfy respective predetermined criteria corresponding to the results of detection, which are stored or set in advance. Then, based on the respective results of determination, the pre-use checker 201 determines whether the laser therapy apparatus 1 used is in a state for conducting appropriate laser therapy. For example, if at least one of the result of detection by the first light amount detector 25, the result of detection by the current detector 23, the result of detection by the temperature detector 26, and the result of detection by the second light amount detector 32 fails to satisfy the predetermined criterion, it is determined that a state where second laser light which is suitable for therapy can be radiated from the laser irradiator 31 does not exist.

Moreover, the pre-use checker 201 performs a process of causing the display 29 to indicate that it has been learned through a pre-use check that the laser therapy apparatus 1 is malfunctioning or that, if it is not malfunctioning, an anomaly has been detected. Furthermore, the pre-use checker 201 outputs to the memory 28 the fact that the pre-use check mode has been executed, as well as a result of the pre-use check. The indication of a malfunctioning or detection of an anomaly may be made in such a manner that it specifically points out which one of the first light amount detector 25, the current detector 23, the temperature detector 26, and the second light amount detector 32 is being abnormal.

In the present embodiment, the pre-use checker 201 performs a pre-use check based on results of detection from the current detector 23, the first light amount detector 25, the temperature detector 26, and the subsequently-described second light amount detector 32; note however that a pre-use check may be performed based on a result of detection from the second light amount detector 32 at the least. The reason is that, even without utilizing the results of detection by the current detector 23 and the first light amount detector 25, if the result of detection by the second light amount detector 32 satisfies the predetermined criterion, it can safely be determined that a state where laser light which is suitable for therapy can be radiated from the irradiation unit 3 exists.

On the other hand, by utilizing results of detection by the current detector 23, the first light amount detector 25, the temperature detector 26, and the subsequently-described second light amount detector 32, it becomes possible to specifically report which component part of the laser therapy apparatus 1 is malfunctioning or which component part has an anomaly.

Moreover, in addition to the aforementioned results of detection, the pre-use checker 201 may be arranged so as to detect anomalies in the general functions of the apparatus other than the function of laser irradiation, e.g., the display 29, the operational interface 21, and the memory 28.

<Pre-Use Check Detector 202>

When the laser therapy apparatus 1 is activated, the pre-use check detector 202 extracts from the memory 28 the data at an activation which was immediately previous (most recent) to the current activation of the laser therapy apparatus 1 (hereinafter referred to as the "preceding activation"), and detects whether the pre-use check mode had been executed at the preceding activation. Then, the pre-use check detector 202 gives the display 29 an instruction to indicate data concerning the detected execution/non-execution of a pre-use check, and if a pre-use check had been performed, the result of the pre-use check, i.e., presence or absence of malfunctioning or anomalies.

Note that, even if a pre-use check had been performed at the preceding activation, if a predetermined period (e.g., 72 hours) or more has passed since the preceding activation and until the current activation, for example, the pre-use check detector 202 may detect absence of a pre-use check, and cause the display 29 to so indicate.

<Memory 28>

When the pre-use check mode is selected by the operational interface 21, based on an output from the pre-use checker 201, the memory 28 stores the fact that the pre-use check mode has been executed as well as data concerning the result of the pre-use check. Moreover, when the laser therapy apparatus 1 is activated, the memory 28 stores the fact that the laser therapy apparatus 1 has been activated, based on an instruction from the controller 27. Then, based on an instruction from the pre-use check detector 202, the memory 28 outputs the stored data concerning the preceding activation to the pre-use check detector 202.

<Irradiation Unit 3>

Figure 4:
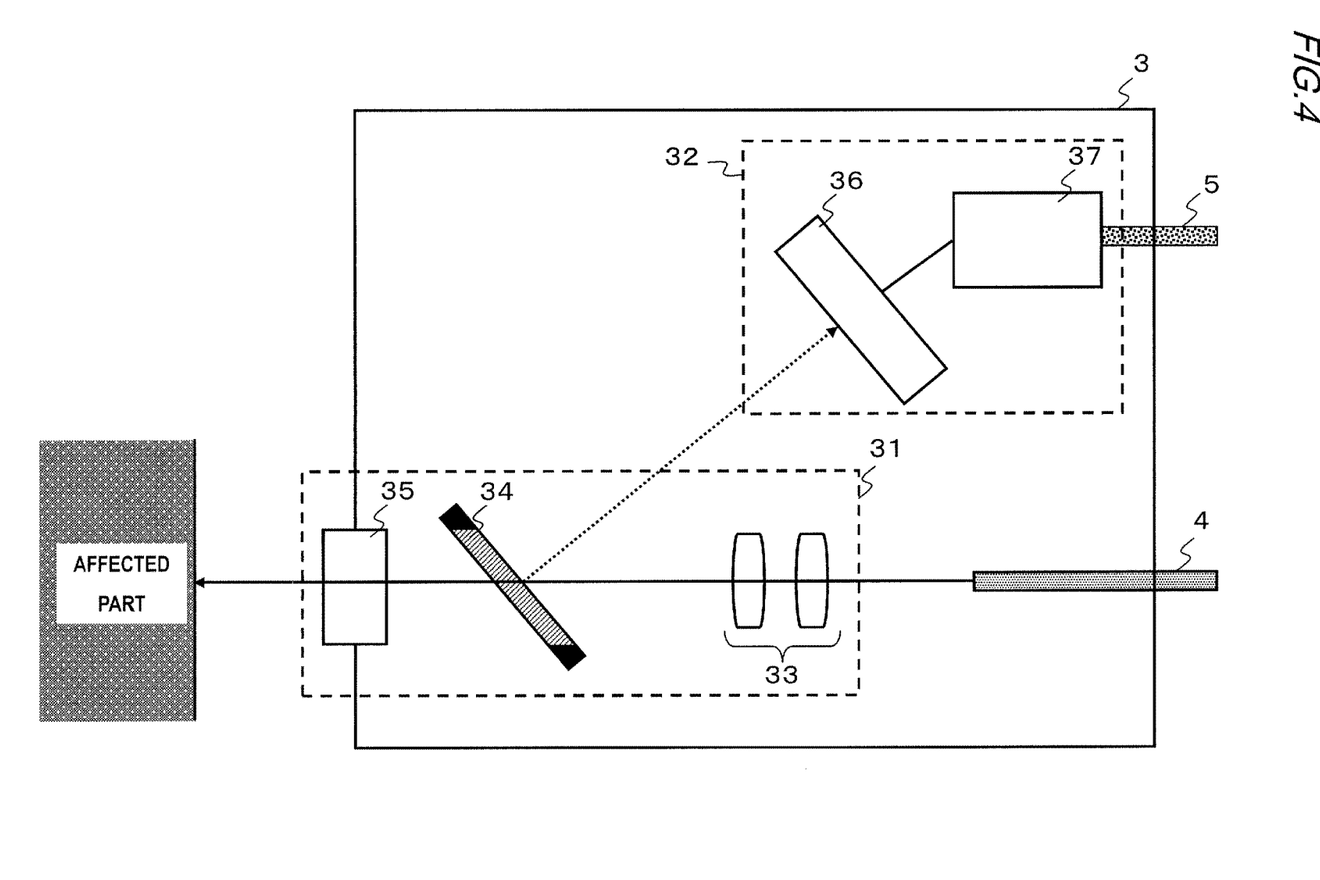
FIG. 4 An example diagram showing the specific construction of an irradiation unit of the laser therapy apparatus according to Embodiment 1 of the present application.

The irradiation unit 3 includes the laser irradiator 31 and the second light amount detector 32, as shown in FIG. 2. FIG. 4 shows an exemplary specific construction of the irradiation unit 3.

<Laser Irradiator 31>

The laser irradiator 31 subjects the first laser light from each of the plurality of light sources in the laser source 24, which has been guided via the light-guiding fiber 4, to at least one of light-guiding and beamforming to thereby convert the first laser light into second laser light, and radiates this second laser light to the affected part.

Specifically, as shown in FIG. 4, the laser irradiator 31 includes an optical lens 33, a beam splitter 34, and an irradiation opening 35. The optical lens 33 gathers the first laser light which has been led along the light-guiding fiber 4, whereby the first laser light is converged into a beam and thus converted into second laser light. Through the irradiation opening 35, the second laser light exits to the exterior of the irradiation unit 3, and is radiated on the affected part as therapeutic light. Moreover, the second laser light is split by the beam splitter 34 so that a portion thereof is led to the second light amount detector 32.

<Second Light Amount Detector 32>

The second light amount detector 32, which includes a photodiode 36 and an I-V (current-voltage) conversion circuit 37, receives the second laser light having been split by the beam splitter 34, and converts it to a voltage value at the I-V (current-voltage) conversion circuit. Then, a signal concerning this voltage value is output to the pre-use checker 201 via the signal cable 5.

<Display 29>

The display 29 displays various setting information and the like. Specifically, for example, the display 29 includes an alert lamp 29a indicating absence of a pre-use check, an alert lamp 29c indicating malfunctioning, an alert lamp 29d indicating anomalies, and a code indicator 29e indicating the details of malfunctioning or anomalies. As a result of this, the user knows the state of the laser therapy apparatus 1, e.g., malfunctioning or anomalies, as well as need for a pre-use check.

In the present embodiment, the result of a pre-use check or an alert indication is reported to the user based on an indication on the display 29; however, the present invention is not limited thereto. For example, the result of a pre-use check or an alert may be displayed on a display device, e.g., a liquid crystal display device, that is capable of displaying arbitrary numbers, text, figures, or images. Alternatively, it may be of a construction where sound notifications are made, e.g., by a buzzer. In other words, there is no particular limitation so long as the alarm permits visual or auditory understanding of the user as to the result of a pre-use check or the need for a pre-use check.

<Light-Guiding Fiber 4>

As described above, the light-guiding fiber 4 is a medium for guiding first laser light which is output from the laser source 24 and supplying it to the laser irradiator 31.

<Signal Cable 5>

The signal cable 5 is a medium for supplying a signal concerning the result of detection by the second light amount detector 32 to the pre-use checker 201.

<Power Cable 6>

The power cable 6 is coupled to external power, and supplies electricity to the laser therapy apparatus 1.

<<Regarding Operation>>

Figure 5:
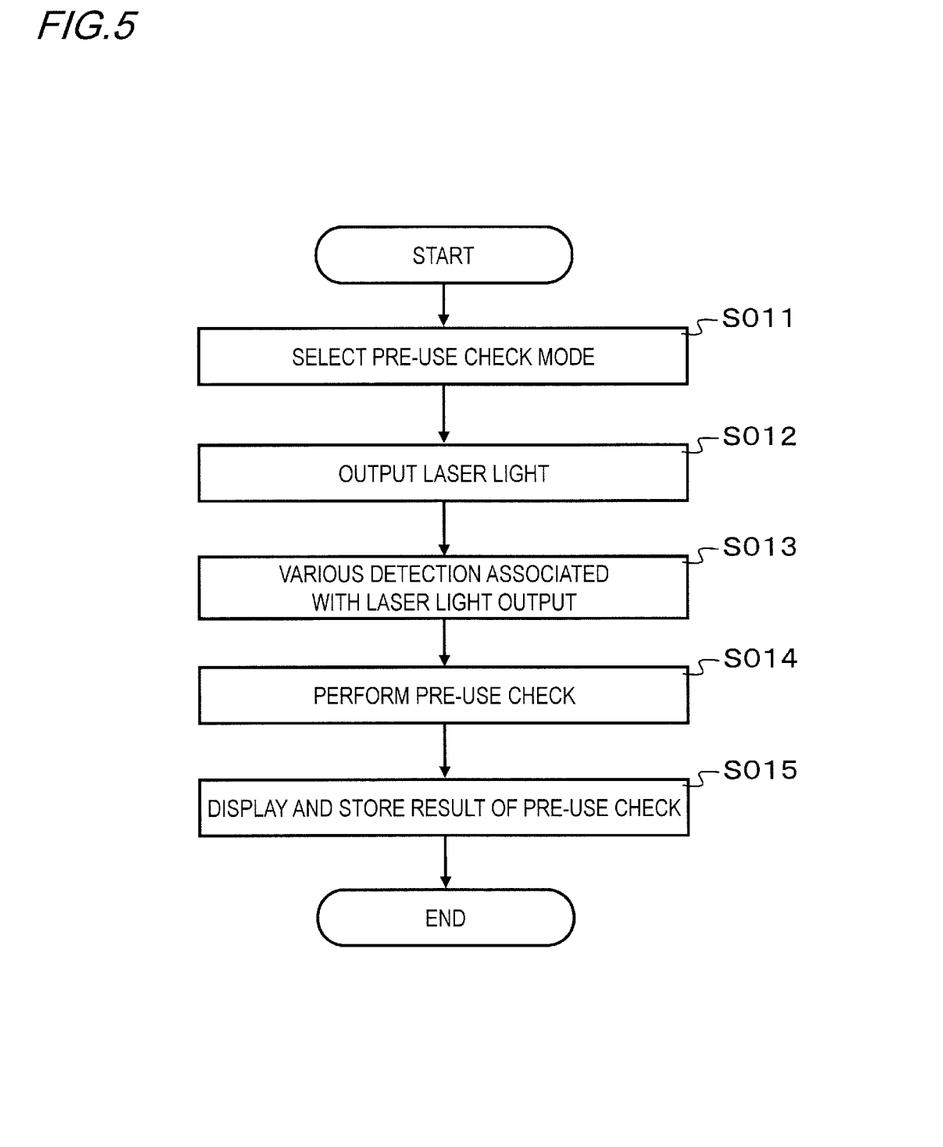
FIG. 5 An example operation flow diagram in the case where a pre-use check mode of the laser therapy apparatus according to Embodiment 1 of the present application is selected.
Figure 6:
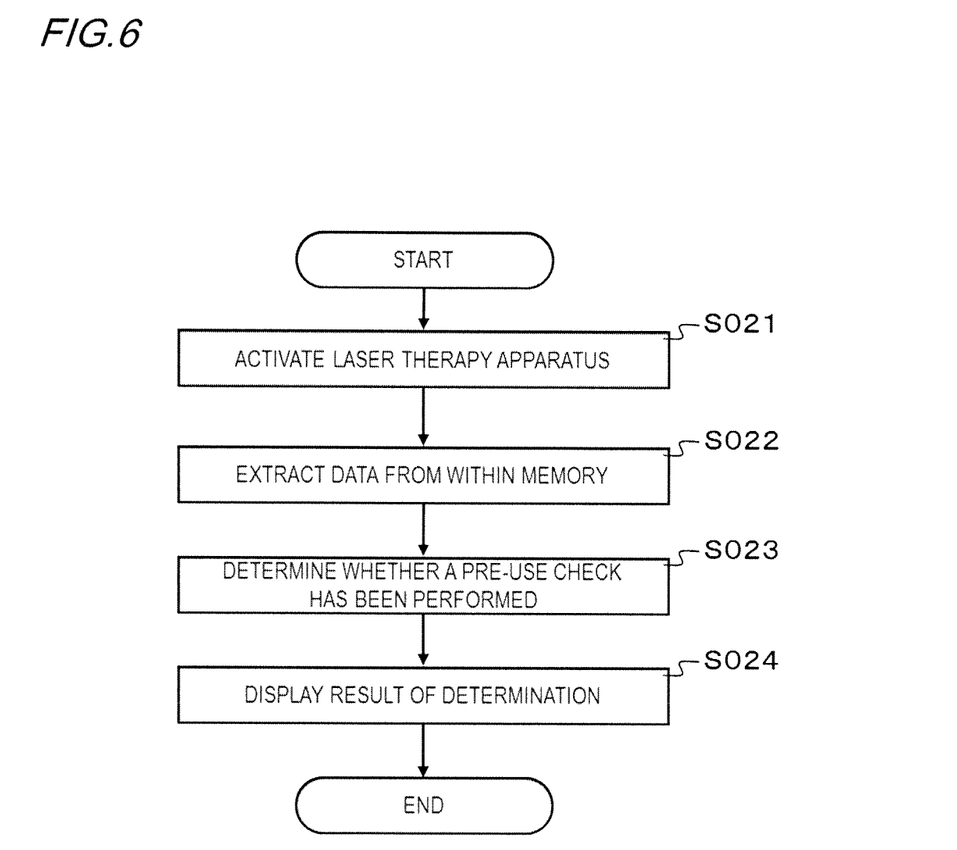
FIG. 6 An example operation flow diagram in the case where the laser therapy apparatus according to Embodiment 1 of the present application is activated.

An operation of the laser therapy apparatus 1 having the above-described construction will be described by using operation flow diagrams of FIG. 5 and FIG. 6, while also touching on the operation by a manipulator. Herein, a case where the pre-use check mode is selected (Step 1 (S011) to Step 5 (S015) corresponding to FIG. 5) and a case where the laser therapy apparatus 1 is activated and operates in the therapy mode (Step 1 (S021) to Step 4 (S024) corresponding to FIG. 6) will each be described.

<Operation Flow of the Case where the Pre-Use Check Mode is Selected>

Hereinafter, an operation of the laser therapy apparatus 1 in the case where the pre-use check mode is selected will be described.

(Step 1 (S011))

At Step 1 (S011), the user manipulates the pre-use check switch 21c to select the pre-use check mode.

(Step 2 (S012))

At Step 2 (S012), the user turns ON the foot switch 21b. As a result of this, the controller 27 causes the laser source 24 to output first laser light of an output level, irradiation time, etc., that correspond to the pre-use check mode, via the current controller 22.

(Step 3 (S013))

At Step 3 (S013), in response to the first laser light being output from the laser source 24, the current detector 23 performs a current value detection, the first light amount detector 25 performs a light amount detection for first laser light, the temperature detector 26 performs a temperature detection for the laser source 24, and the second light amount detector 32 performs a light amount detection for second laser light. Then, the results of detection as detected by the respective blocks are output to the pre-use checker 201.

(Step 4 (S014))

At Step 4 (S014), based on the respective results of detection from Step 3 (S013), the pre-use checker 201 performs a pre-use check.

The specific pre-use check is described below. The pre-use checker 201 possesses predetermined criteria corresponding to the result of detection by the current detector 23, the result of detection by the first light amount detector 25, the result of detection by the temperature detector 26, and the result of detection by the second light amount detector 32. For example, these predetermined criteria may be predetermined threshold values or predetermined threshold ranges. Then, the pre-use checker 201 makes determinations as to whether the results of detection by the respective blocks (current detector 23, first light amount detector 25, temperature detector 26, second light amount detector 32) satisfy the respective predetermined criteria corresponding thereto.

If the pre-use checker 201 determines that the result of detection by the second light amount detector 32 does not satisfy the predetermined criterion, it means that, even if laser therapy were to be subsequently performed, second laser light of a predetermined output level corresponding to that laser therapy would not be radiated onto the affected part. Therefore, in this case, the pre-use checker 201 determines that the laser therapy apparatus 1 is "malfunctioning", and turns on the alert lamp 29c indicating malfunctioning.

On the other hand, if the pre-use checker 201 determines that, although the result of detection by the second light amount detector 32 satisfies the predetermined criterion, at least one of the result of detection by the current detector 23, the result of detection by the first light amount detector 25, and the result of detection by the temperature detector 26 does not satisfy the predetermined criterion regarding at least one light source among the plurality of light sources provided in the laser source 24, then the pre-use checker 201 determines an "anomaly" of the laser therapy apparatus 1, and turns on the alert lamp 29d indicating anomalies. The reason is that, even if the laser irradiator 31 may be appropriately radiating second laser light, the fact that at least one of the result of detection by the current detector 23, the result of detection by the first light amount detector 25, and the result of detection by the temperature detector 26 does not satisfy the predetermined criterion means that redundancy is not provided by the plurality of light sources in the laser source 24, leading to a possibility of anomalies of the laser therapy apparatus 1, e.g., malfunctioning, when subsequently conducting laser therapy.

When the aforementioned malfunction/anomaly determinations have been made, the pre-use checker 201 causes the code indicator 29e to display the details of malfunctioning or anomalies, which indicate which component part is suffering from malfunctioning or anomalies.

On the other hand, if the pre-use checker 201 determines that the result of detection by the current detector 23, the result of detection by the first light amount detector 25, and the results of detection by the temperature detector 26 and the second light amount detector 32 all satisfy the predetermined criteria for every one of the plurality of light sources provided in the laser source 24, then the pre-use checker 201 determines that there is no "malfunctioning" or "anomalies".

(Step 5 (S015))

At Step 5 (S015), the pre-use checker 201 causes the display 29 to display the result of a pre-use check, and causes the memory 28 to store the fact that the pre-use check mode has been executed as well as a result of the pre-use check, thus terminating the pre-use check mode. Termination of the pre-use check mode may be automatically made by the pre-use checker 201 after the aforementioned operation of the pre-use checker 201, and the therapy mode may take over, for example. Alternatively, after the pre-use check mode is terminated, the therapy mode may be entered as the user manipulates the operational interface 20. Alternatively, a state of being able to operate in the therapy mode may be entered as the user turns OFF the power switch 21a and again turns ON the power switch 21a.

<Operation Flow of the Case where the Laser Therapy Apparatus 1 is Activated>

Hereinafter, an operation of the laser therapy apparatus 1 in the case where the laser therapy apparatus 1 is activated will be described.

(Step 1 (S021))

At Step 1 (S021), the user manipulates the power switch 21a to activate the laser therapy apparatus 1. As a result, the laser therapy apparatus 1 enters a state of being able to operate in the therapy mode.

(Step 2 (S022))

At Step 2 (S022), from within the data in the memory 28, the pre-use check detector 202 extracts data concerning the preceding activation.

(Step 3 (S023))

At Step 3 (S023), the pre-use check detector 202 determines whether a pre-use check was performed at the preceding activation of the laser therapy apparatus 1 or not.

(Step 4 (S024))

At Step 4 (S024), the pre-use check detector 202 determines whether a use check was performed at the preceding activation of the laser therapy apparatus 1 or not, and if a pre-use check was indeed performed, gives an instruction for causing the result of a pre-use check to be displayed. Specifically, for example, if a pre-use check was performed at the preceding activation, the pre-use check detector 202 does not turn on the alert lamp 29a for indicating absence of a pre-use check. Because the alert lamp 29a for indicating absence of a pre-use check is not turned on, the user knows that an appropriate pre-use check has been performed.

On the other hand, if no pre-use check was performed at the preceding activation, the pre-use check detector 202 turns on the alert lamp 29a for indicating absence of a pre-use check. Because the alert lamp 29a for indicating absence of a pre-use check is turned on, the user knows that no appropriate pre-use check has been performed.

The user confirms these indications to determine whether or not to conduct laser therapy.

<<Summary>>

As described above, with the laser therapy apparatus according to an embodiment of the present invention, it is possible to confirm whether the laser therapy apparatus has undergone an appropriate pre-use check, when conducting laser therapy. Thus, the pre-use check can reduce the possibility of the laser therapy apparatus malfunctioning during laser therapy.

Other Embodiments

In the above embodiment, the pre-use check detector 202 only determines whether a pre-use check was performed at the preceding, i.e., immediately previous, activation; however, the pre-use check detector 202 may determine whether a pre-use check was performed at a plurality of past activations including the immediately previous activation of the current activation, and cause the display 29 to display the results of determination.

Specifically, it may be determined whether a pre-use check was performed at a predetermined plurality of (e.g. three) consecutive past activations including the immediately previous activation of the current activation. Alternatively, it may be determined whether a pre-use check was performed at a plurality of past activations, including the immediately previous activation of the current activation, which were made within a predetermined past period (e.g., within 72 hours) from the current activation.

For example, it may be possible that, after a pre-use check was performed at a certain activation and until an activation is made for conducting therapy by using the laser therapy apparatus 1, the laser therapy apparatus 1 may be powered ON and then powered OFF one or more times, without even performing a pre-use check or an operation in the therapy mode. In this case, although a pre-use check was not performed at the preceding activation, no significant changes have presumably occurred in the states of the respective elements of the laser therapy apparatus 1 until the current time since the most recent pre-use check.

Therefore, in such a case, the pre-use check detector 202 may check whether a pre-use check was performed at any activation among a predetermined plurality of consecutive past activations, or among a plurality of past activations which were made within a predetermined past period from the current activation, and if a pre-use check was indeed performed, determine that a use check corresponding to the current activation has been performed.

Moreover, in a scenario as above where a pre-use check was not performed at the immediately previous activation, it may be possible for some reason that second laser light may be emitted from the irradiation unit 3, although not for a pre-use check, between the most recent pre-use check and the current activation.

In such a case, as a criterion for determining whether a pre-use check has been performed, the pre-use check detector 202 may rely on the fact as to whether second laser light has been radiated or not. For example, the pre-use check detector 202 may determine that a pre-use check corresponding to the current activation has been performed if a pre-use check has been performed but if second laser light has not been radiated, at any activation among a predetermined plurality of consecutive past activations, or among a plurality of past activations which were made within a predetermined past period from the current activation.

Moreover, even if second laser light has been radiated once or a plurality of times, hardly any deterioration in the light sources will have occurred if the total irradiation time was short. In this case, it may be similarly determined that a pre-use check corresponding to the current activation has been performed. On the other hand, if the total irradiation time of second laser light is equal to or greater than a predetermined value, it is considered that after the preceding pre-use check there has been an operation in which deteriorations in the performance of the light sources, etc., may have occurred. In this case, it may be determined that a pre-use check corresponding to the current activation has not been performed.

INDUSTRIAL APPLICABILITY

The present invention is applicable to various therapeutic apparatuses and diagnostic apparatuses, and is suitably used for therapeutic apparatuses and diagnostic apparatuses which can reduce the possibility of malfunctioning or the like during therapy or diagnosis, thus being able to perform appropriate operations.

REFERENCE SIGNS LIST

1 laser therapy apparatus
2 main body
3 irradiation unit
4 light-guiding fiber
5 signal cable
6 power cable
21, 21a, 21b operational interface
22 current controller
23 current detector
24 laser source
25 first light amount detector
26 temperature detector
27 controller
28 memory
29 display
201 pre-use checker
202 pre-use check detector

The invention claimed is:

1. A laser therapy apparatus comprising:
a laser source including at least one light source that outputs first laser light;
a laser irradiator that subjects the first laser light to at least one of light-guiding and beamforming to convert the first laser light into second laser light, and radiating the second laser light to the exterior;
a second light amount detector that detects a light amount of second laser light;
a pre-use checker that performs a pre-use check at least based on a result of detection by the second light amount detector;
a pre-use check detector that determines whether a pre-use check corresponding to a current activation has been performed or not, based on past-activation information and a result of the pre-use check by the pre-use checker; and an alarm that reports, at the current activation, a result of determination by the pre-use check detector, wherein, the past-activation information is information of an immediately previous activation of the current activation; and the pre-use check detector determines whether the pre-use check has been performed or not based on information of the immediately previous activation of the current activation.

2. The laser therapy apparatus of claim 1, wherein, the pre-use check detector determines that a pre-use check corresponding to the current activation has been performed if the pre-use check was performed at the immediately previous activation of the current activation, and that a pre-use check corresponding to the current activation has not been performed if the pre-use check was not performed at the immediately previous activation of the current activation.

3. The laser therapy apparatus of claim 1, wherein the pre-use check detector determines that no pre-use check corresponding to the current activation has been performed if a predetermined period or more has elapsed since the immediately previous activation and until the current activation, regardless of whether the pre-use check was performed at the immediately previous activation or not.

4. The laser therapy apparatus of claim 1, wherein, if the result of detection by the second light amount detector satisfies a predetermined criterion which is provided in advance, the pre-use checker determines that a state exists where second laser light suitable for therapy is emittable from the laser irradiator.

5. The laser therapy apparatus of claim 1, wherein the pre-use check by the pre-use checker comprises a check as to whether a state exists where second laser light suitable for therapy is emittable from the laser irradiator.

6. The laser therapy apparatus of claim 1, wherein the pre-use checker determines that the laser therapy apparatus is malfunctioning if the result of detection by the second light amount detector does not satisfy a predetermined criterion which is provided in advance.

7. The laser therapy apparatus of claim 1, further comprising a first light amount detector that detects a light amount of first laser light, wherein the pre-use check by the pre-use checker comprises a check as to whether a result of detection by the first light amount detector satisfies a predetermined criterion which is provided in advance.

8. The laser therapy apparatus of claim 1, further comprising a current detector that detects a current value of an electric current which is supplied to the light source, wherein the pre-use check by the pre-use checker comprises a check as to whether a result of detection by the current detector satisfies a predetermined criterion which is provided in advance.

9. The laser therapy apparatus of claim 1, further comprising a temperature detector that detects a temperature of the light source, wherein the pre-use check by the pre-use checker comprises a check as to whether a result of detection by the temperature detector satisfies a predetermined criterion which is provided in advance.

10. The laser therapy apparatus of claim 1, further comprising:

a first light amount detector that detects a light amount of first laser light;

a current detector that detects a current value of an electric current which is supplied to the light source; and a temperature detector that detects a temperature of the light source, wherein the pre-use checker determines that the laser therapy apparatus has an anomaly if at least one of a result of detection by the first light amount detector, a result of detection by the current detector and a result of detection by the temperature detector does not satisfy the predetermined criterion.

11. The laser therapy apparatus of claim 1, further comprising an operational interface that sets laser light output from the laser source ON or OFF.

12. The laser therapy apparatus of claim 11, wherein the pre-use checker controls the laser source so as to output first laser light with a predetermined period and a predetermined output level when laser light output is set ON by the operational interface, and performs the pre-use check based on information during the predetermined period.

13. The laser therapy apparatus of claim 1, wherein the laser source includes a plurality of light sources, and outputs the first laser light from each of the plurality of light sources.

14. The laser therapy apparatus of claim 1, wherein the pre-use check detector causes the alarm to report the check result of the pre-use check together with the result of determination by the pre-use check detector.

15. A laser therapy apparatus comprising:

a laser source including at least one light source that outputs first laser light;

a laser irradiator that subjects the first laser light to at least one of light-guiding and beamforming to convert the first laser light into second laser light, and radiating the second laser light to the exterior;

a second light amount detector that detects a light amount of second laser light;

a pre-use checker that performs a pre-use check at least based on a result of detection by the second light amount detector;

a pre-use check detector that determines whether a pre-use check corresponding to a current activation has been performed or not, based on past-activation information and a result of the pre-use check by the pre-use checker; and an alarm that reports, at the current activation, a result of determination by the pre-use check detector, wherein, the past-activation information is information of a predetermined plurality of consecutive past activations including the immediately previous activation of the current activation; and the pre-use check detector determines whether a pre-use check corresponding to the current activation has been performed or not based on information of the plurality of past activations.

16. The laser therapy apparatus of claim 15, wherein the pre-use check detector determines whether a pre-use check corresponding to the current activation has been performed or not based on whether the second laser light was radiated between the activation among the plurality of past activations at which the pre-use check was performed and the current time.

17. The laser therapy apparatus of claim 15, wherein the pre-use check detector determines whether a pre-use check corresponding to the current activation has been performed or not based on a total length of time for which the second laser light was radiated between the activation among the plurality of past activations at which the pre-use check was performed and the current time.

18. A laser therapy apparatus comprising:
- a laser source including at least one light source that outputs first laser light;
- a laser irradiator that subjects the first laser light to at least one of light-guiding and beamforming to convert the first laser light into second laser light, and radiating the second laser light to the exterior;
- a second light amount detector that detects a light amount of second laser light;
- a pre-use checker that performs a pre-use check at least based on a result of detection by the second light amount detector;
- a pre-use check detector that determines whether a pre-use check corresponding to a current activation has been performed or not, based on past-activation information and a result of the pre-use check by the pre-use checker; and
- an alarm that reports, at the current activation, a result of determination by the pre-use check detector, wherein,
- the past-activation information is information of a plurality of past activations including the immediately previous activation of the current activation which were made within a predetermined past period from the current activation; and
- the pre-use check detector determines whether a pre-use check corresponding to the current activation has been performed or not based on information of the plurality of past activations.

* * * * *